United States Patent
Tian et al.

(10) Patent No.: US 10,573,201 B2
(45) Date of Patent: Feb. 25, 2020

(54) METHOD OF PRODUCING A PHANTOM AND PHANTOM

(71) Applicant: MAX-PLANCK-GESELLSCHAFT ZUR FÖRDERUNG DER WISSENSCHAFTEN E.V., Munich (DE)

(72) Inventors: Qiu Tian, Stuttgart (DE); Peer Fischer, Freiburg (DE)

(73) Assignee: MAX-PLANCK-GESELLSCHAFT ZUR FÖRDERUNG DER WISSENSCHAFTEN E.V. (DE)

( * ) Notice: Subject to any disclaimer, the term of this patent is extended or adjusted under 35 U.S.C. 154(b) by 212 days.

(21) Appl. No.: 15/608,251

(22) Filed: May 30, 2017

(65) Prior Publication Data

US 2018/0130381 A1 May 10, 2018

(30) Foreign Application Priority Data

May 30, 2016 (EP) ..................................... 16172019

(51) Int. Cl.
*G09B 23/28* (2006.01)
*G09B 23/34* (2006.01)
(Continued)

(52) U.S. Cl.
CPC .............. *G09B 23/34* (2013.01); *A61B 6/032* (2013.01); *A61B 6/583* (2013.01); *B29C 33/3835* (2013.01); *B29C 33/3842* (2013.01); *B29C 39/00* (2013.01); *B29C 39/006* (2013.01); *B29C 39/10* (2013.01); *B29C 64/00* (2017.08); *B33Y 70/00* (2014.12); *B33Y 80/00* (2014.12); *G09B 9/00* (2013.01); *G09B 23/285* (2013.01);
(Continued)

(58) Field of Classification Search
USPC ................................ 434/262, 267, 268, 272
See application file for complete search history.

(56) References Cited

U.S. PATENT DOCUMENTS 5,055,051 A * 10/1991 Duncan .................. G09B 23/28
434/262
5,945,056 A 8/1999 Day et al.
(Continued)

FOREIGN PATENT DOCUMENTS

WO 2014173579 A1 10/2014

OTHER PUBLICATIONS

Allard et al.; "A Multimodality Vascular Imaging Phantom of an Abdominal Aortic Aneurysm with a Visible Thrombus"; retrieved from internet; URL http://lbum-crchum.com/publications-fichiers/w134-Med-Phys-2013-Allard.pdf; 2013; 10 pgs.
(Continued)

*Primary Examiner* — Kurt Fernstrom

(57) ABSTRACT

The present invention relates to a method of producing a phantom resembling a human or animal organ or tissue, the phantom comprising at least one first region having at least one tissue like property and at least one cavity having a plurality of hollow branches connected thereto, with at least some of the plurality of hollow branches being formed such that they project into the first region having tissue like properties. The invention further relates to a method of making the first structure and to a corresponding phantom.

19 Claims, 7 Drawing Sheets

Figure 3:
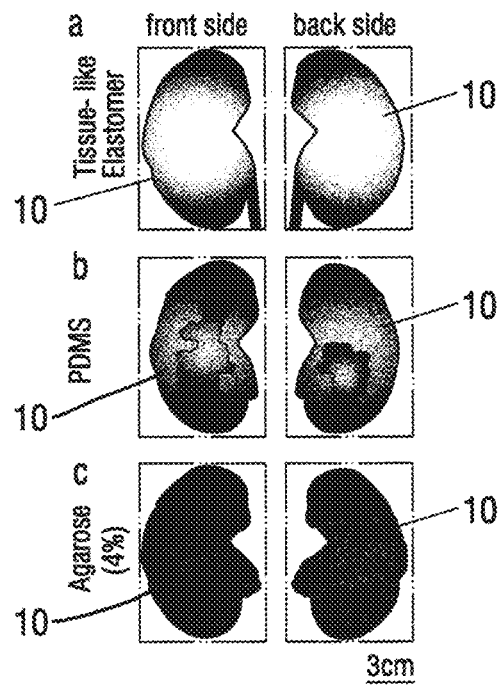

(51) Int. Cl.

| | | |
|---|---|---|
| *B29C 33/38* | (2006.01) | |
| *B33Y 80/00* | (2015.01) | |
| *B29C 39/00* | (2006.01) | |
| *B29C 64/00* | (2017.01) | |
| *B33Y 70/00* | (2020.01) | |
| *A61B 6/03* | (2006.01) | |
| *A61B 6/00* | (2006.01) | |
| *B29C 39/10* | (2006.01) | |
| *G09B 9/00* | (2006.01) | |
| *B29L 31/00* | (2006.01) | |
| *B29K 83/00* | (2006.01) | |
| *B33Y 10/00* | (2015.01) | |
| *B29C 64/112* | (2017.01) | |
| *B29C 64/393* | (2017.01) | |

(52) U.S. Cl.
CPC ......... *G09B 23/286* (2013.01); *B29C 64/112* (2017.08); *B29C 64/393* (2017.08); *B29K 2083/00* (2013.01); *B29K 2083/005* (2013.01); *B29K 2995/0062* (2013.01); *B29L 2031/702* (2013.01); *B29L 2031/7028* (2013.01); *B29L 2031/7532* (2013.01); *B33Y 10/00* (2014.12)

(56) References Cited

U.S. PATENT DOCUMENTS

| | | | |
|---|---|---|---|
| 6,474,993 B1 | 11/2002 | Grund et al. | |
| 6,511,325 B1* | 1/2003 | Lalka | A61B 8/587 |
| | | | 434/267 |
| 7,059,168 B2 | 6/2006 | Hibi et al. | |
| 7,255,565 B2* | 8/2007 | Keegan | G09B 23/286 |
| | | | 434/267 |
| 7,419,376 B2 | 9/2008 | Sarvazyan et al. | |
| 8,480,407 B2* | 7/2013 | Campbell | G09B 23/28 |
| | | | 434/272 |
| 8,911,238 B2* | 12/2014 | Forsythe | G09B 23/28 |
| | | | 434/267 |
| 2008/0076101 A1* | 3/2008 | Hyde | G09B 23/30 |
| | | | 434/272 |
| 2009/0226867 A1 | 9/2009 | Kalafut et al. | |
| 2010/0047752 A1 | 2/2010 | Chan et al. | |
| 2010/0196867 A1* | 8/2010 | Geerligs | G09B 23/28 |
| | | | 434/272 |
| 2012/0148994 A1 | 6/2012 | Hori et al. | |
| 2012/0189998 A1 | 7/2012 | Kruecker et al. | |
| 2012/0282584 A1 | 11/2012 | Millon et al. | |
| 2013/0059280 A1 | 3/2013 | Haverich | |
| 2014/0106329 A1* | 4/2014 | Watanabe | G09B 23/30 |
| | | | 434/272 |
| 2015/0037775 A1* | 2/2015 | Ottensmeyer | G09B 23/34 |
| | | | 434/271 |
| 2016/0027341 A1* | 1/2016 | Kerins | G09B 23/34 |
| | | | 434/270 |
| 2016/0027344 A1 | 1/2016 | Felsinger et al. | |
| 2016/0148541 A1* | 5/2016 | Ristolainen | G09B 23/30 |
| | | | 434/268 |

OTHER PUBLICATIONS

Bernhard; "Personalized 3D Printed Model of Kidney and Tumor Anatomy: a Useful Tool for Patient Education"; Springer-Verlag Berlin Heidelberg; 2015; 9 pages.

Blankstein et al.; "Simulation-Based Flexible Ureteroscopy Training Using a Novel Ureteroscopy Part-Task Trainer"; retrieved from CUAJ; Sep.-Oct. 2015, vol. 9, Issues 9-10 © 2015 Canadian Urological Association; 5 pages.

Cheung et al.; "Use of 3-Dimensional Printing Technology and Silicone Modeling in Surgical Simulation: Development and Face Validation in Pediatric Laparoscopic Pyeloplasty"; Journal of Surgical Education; vol. 71, No. 5; 2014; 6 pages.

Golden et al.; "Fabrication of Microfluidic Hydrogels Using Molded Gelatin as a Sacrificial Element"; Lab on a Chip, vol. 7, No. 6, Mar. 2007; 6 pages.

Kang et al.; "A 3D Bioprinting System to Produce Human-Scale Tissue Constructs with Structural Integrity"; Nature Biotechnology, vol. 24, No. 3, Feb. 15, 2016; 12 pages.

Kolesky et al.; "3D Bioprinting of Vascularized, Heterogeneous Cell-Laden Tissue Constructs"; Advanced Materials; vol. 26, No. 19, May 2014; 8 pages.

Kurenov et al.; "Three-Dimensional Printing to Facilitate Anatomic Study, Device Development, Simulation, and Planning in Thoracic Surgery"; Journal of Thoracic and Cardiovascular Surgery; vol. 149, No. 4, Apr. 2015; 8 pages.

Official Communication from European Patent Office for related European Application No. 16172019.8; dated Sep. 29, 2016; 5 pages.

Ristolainen; "Economically Affordable Anatomical Kidney Phantom with Calyxes for Puncture and Drainage Training in Interventional Urology and Radiology"; Acta Radiologica Short Reports 3(5) 1-7 © The Foundation Acta Radiologica; 2014; 7 pages.

Turney; "A New Model with an Anatomically Accurate Human Renal Collecting System for Training in Fluoroscopy-Guided Percutaneous Nephrolithotomy Access"; Journal of Endourology, vol. 28, No. 3, Mar. 2014; 5 pages.

\* cited by examiner

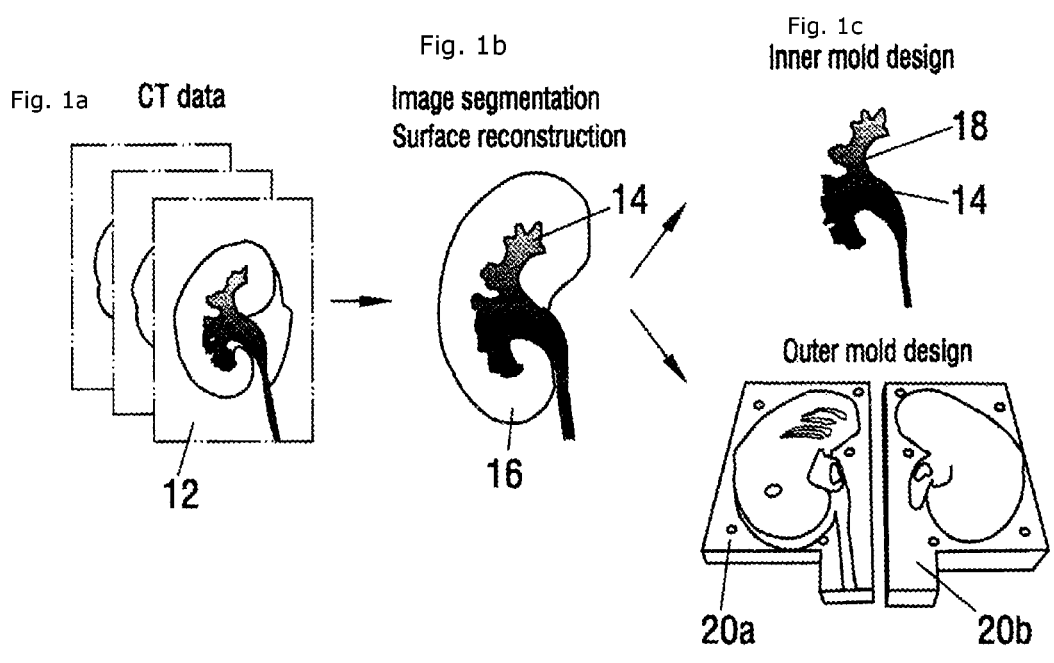
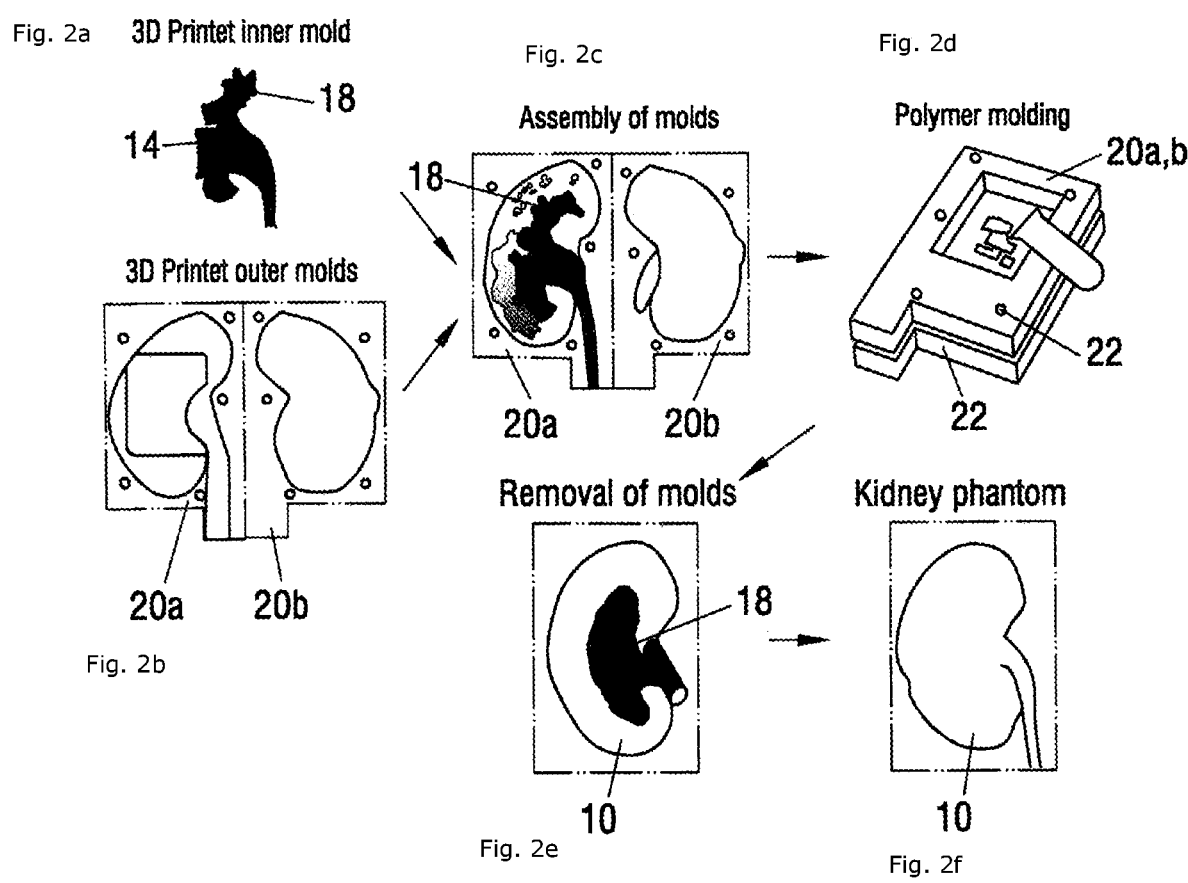

Fig.9
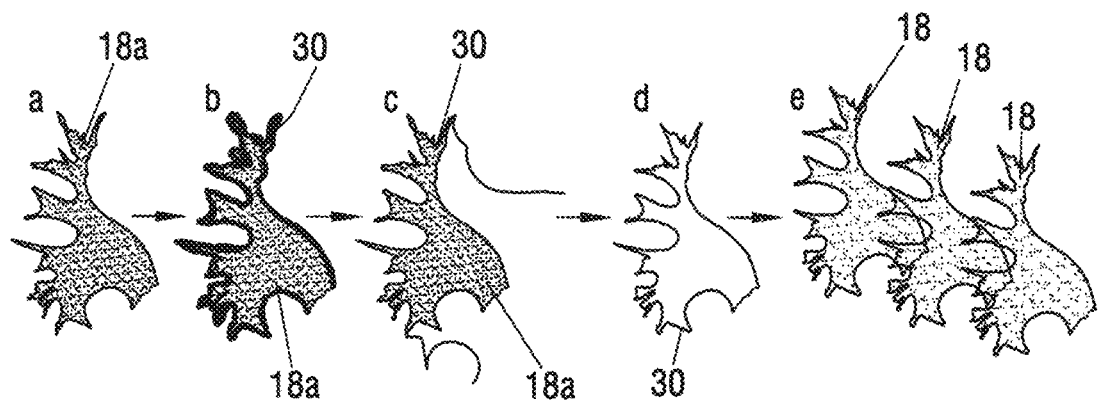
a  3D printed collecting system
b  Glove mold
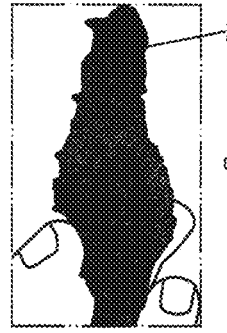
c  paraffin
d  gelatin
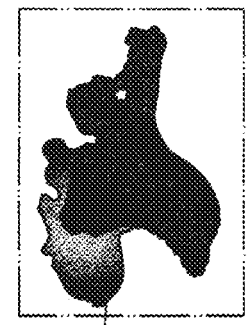
Fig.10

METHOD OF PRODUCING A PHANTOM AND PHANTOM

The present invention relates to a method of producing a phantom resembling a human or animal organ or tissue, the phantom comprising at least one first region having at least one tissue like property and at least one cavity having a plurality of hollow branches connected thereto, with at least some of the plurality of hollow branches being formed such that they project into the first region having tissue like properties; and to a corresponding phantom.

The production of anatomically correct body parts, such as organs or joints, is known. These body parts are typically used by surgeons and/or teachers in order to explain the function of the body part concerned and where a possible defect, e.g. a ruptured ligament or a tumor, could be present in that body part and why this defect needs to be addressed.

However, these models are typically made from rigid plastic materials and thus do not convey any sense of what that body part may feel like when an operation is conducted thereon.

Moreover, when the concerned body part has a cavity present therein, such as a blood vessel, this is not typically formed as a hollow space, but rather is formed by a block of material. Thus, this kind of anatomically correct model of a body part cannot be used in the training of surgeons and students of medicine on how to perform medical procedures, such as surgery or diagnostic procedures on said body part using medical implants.

Rather surgical training aids are known for this purpose that can be used in the training of surgeons. These training aids typically have an outer shape that resembles that of the concerned body part; however, the cavities formed therein are typically formed by at least one balloon and hence are not produced to a high degree of anatomical correctness, so that e.g. for radiological training purposes, e.g. calyces in a kidney cannot readily be identified.

Moreover, these training aids are frequently not made from a material that permit a surgeon to obtain a correct feel of the organ as the elastic modulus of the materials used to make these phantoms differs from that of the real organ.

For this reason it is an object of the present invention to provide an anatomically correct phantom that not only has an anatomically correct outer shape, but that also includes anatomically correct internal structures, such as cavities, so that the phantoms can reliably be used as surgical training aids. It is a further object of the present invention to provide an anatomically correct phantom that also replicates at least some of the properties of the concerned organ. It is a further object of the present invention to make available a method of manufacture that is less demanding in effort and cost.

These objects are satisfied by a method of manufacturing a phantom and by a corresponding phantom as described herein.

In accordance with the invention such a method of producing a phantom resembling a human or animal organ or tissue, in which the phantom comprises at least one first region having at least one tissue like property and at least one cavity having a plurality of hollow branches connected thereto, with at least some of the plurality of hollow branches being formed such that they project into the first region having tissue like properties, comprises the steps of:

making at least a first structure having a shape that resembles the shape of the at least one cavity and of the interior of the plurality of branches connected to the at least one cavity;

placing said first structure in a phantom mold having an inner shape that resembles an outer shape of the phantom;

filling the phantom mold with a material that has the at least one tissue like property to form the phantom;

removing the first structure from the phantom in order to form the one cavity having a plurality of hollow branches connected thereto within the phantom.

By providing a first structure that is anatomically correct within a mold that forms an anatomically correct outer shape of the phantom, a phantom can be made available that not only has an anatomically correct outer shape but also a phantom that has an anatomically correct internal shape.

Such a method of manufacture is simple to realize, as e.g. the phantom mold can be re-used a plurality of times.

Preferably the step of making the at least one first structure comprises the step of preparing image data from a medical imaging device, preferably CT image data, of a real animal or human organ and designing the first structure in accordance with the obtained image data. Preferably in such a way that the limitation in the resolution of the first structure is defined by the spatial resolution of the medical imaging device used to provide the image data relating to the first structure. It should be noted in this regard that the medical imaging data can be provided by at least one of an MRI device, a CT scanner, a PET, an X-ray device and an ultrasound device.

Similarly the phantom mold can also be designed with reference to data on the concerned real organ obtained using medical imaging devices.

Preferably the method further comprises the step of:

providing at least one second structure in the phantom mold, with the at least one second structure being selected from the group of members consisting of at least one tumor, a transient region, at least one stone, such as a kidney stone, structures that form at least one blood vessel or a network of interconnected blood vessels, structures that form a further cavity, models of nerves or interconnected nerves, a prosthesis or at least one medical implant, with the material of the at least one second structure preferably being selected as at least one of water insoluble and water soluble.

Thereby not only can an anatomically correct phantom be provided, but a phantom can be provided that incorporates a tumor, so that e.g. a surgeon can practice a tumor removing surgical procedure on the phantom.

Moreover, the tumor can also be provided with different material properties such that the phantom can also be used in the diagnostic training of e.g. radiologists.

Advantageously the step of removing the first structure from the phantom is carried out by the application of at least one of heat, the use of a solvent and due to difference in reactivity between the first material and the material of the phantom.

Using e.g. a wax material or a low melting point metal, such as Gallium, to form the first and optionally second structures means that they can be removed on the application of heat and only optionally on the application of a solvent, such that water based compounds can be used to form the material of the phantom. Water based compounds typically have properties that resemble those of human organs as these typically comprise between 70 and 98% water. Materials with different melting points can be used to form the first structure and the second structure respectively, and the differences in temperature facilitates the sequential removal of the materials. Thus, cavities of the first and the second structures are left and are molded by different materials.

Using e.g. Calcium carbonate as the material to form the first structure, so that the first structure can be removed due to its reactivity with an acid solution to form soluble products and gas, but the materials of the phantom and the second structure can be remained intact, e.g. due to their low reactivity to acid.

In this way the first and second structures could respectively be provided in the form of a wax insert that can be removed from the phantom. Alternatively only the first structure is made from a water insoluble material, e.g. wax, and the second structure is also formed from a water soluble material in order to e.g. mimic a tumor.

It could also be advantageous if a melting temperature of the second structure is different from a melting temperature of the first structure. In this way cavities could be formed within the phantom that have different material properties of their walls, as these are heated to higher or lower temperatures. In this way e.g. blood vessels could be formed within the phantom that have a higher degree of elasticity in their wall structure compared to e.g. regions that should resemble nerves or other kinds of cavities.

In this connection it is preferred if the material of the first structure is water insoluble, e.g. a wax, a low melting point metal, such as Gallium, and the material having the at least one tissue like property is water soluble, e.g. agarose gel, gelatin, collagen, elastin, PEG (Polyethylene glycol).

It is preferred if at least one of the phantom mold, the first structure and the second structure is formed using a 3D printer.

3D printers can be used to produce small scale structures and can therefore be used to manufacture anatomically correct structures resembling parts of a human or animal body. The resolution of the insert or mold forming the insert or the outer shape of the phantom is then defined by the resolution of the 3D printer used. This is typically better than the resolution of the image data taken to design the respective part, e.g. first structure, second structure or phantom mold.

Advantageously at least one of the first and the second structures is formed in a mold. Forming structures embedded in the phantom in a mold means that these can be produced in a very cost effective and time effective manner. This is because the material of the structure can e.g. simply be poured into a mold solidify there and then be removed from the mold. Moreover, the use of molds also makes the production of the structures less time consuming and highly reproducible.

It is preferred if the first structure is manufactured with an average root mean square error of less than 2 mm, preferably of less than 0.5 mm. In this way an anatomically correct first structure can be obtained. And as the first structure is inserted into a mold and subsequently removed from the mold anatomically correct cavities can thereby be formed within the phantom.

Preferably the first structure is designed on the basis of data obtained from a CT scanner to this end and the finished first structure and/or phantom is likewise scanned using a CT scanner, with the image data of the scanned first structure being compared to the image data used to design the first structure in order to obtain data on the average root mean square error.

It should be noted in this regard that other medical imaging devices, such as MRI, PET, Ultrasound and X-Ray could also be used to design the shape of the first structure of the phantom mold or of the second structure.

Advantageously the material that has the at least one tissue like property is selected such that the at least one tissue like property reproduces at least one of a mechanical property, an imaging contrast in MRI, CT, X-ray or Ultrasound, an optical property, a visual appearance, a tissue's or organ's absorbance of electromagnetic radiation, a tissue's or organ's absorbance of acoustic waves, a haptic property of the tissue or organ, and an elastic modulus of the corresponding tissue found in the organ.

The same material properties can also be selected for the second structure that is embedded into the phantom if this is to be e.g. a tumor. Thus, a material used for the second structure has at least one property that reproduces at least one of a mechanical property, an imaging contrast in MRI, CT, X-ray or Ultrasound, an optical property, a visual appearance, a tissue's or organ's absorbance of electromagnetic radiation, a tissue's or organ's absorbance of acoustic waves, a haptic property of the tissue or organ, and an elastic modulus of the corresponding tissue or defect, e.g. tumor, found in the organ.

By including at least one material or mixtures of material that comprise at least some of these properties, the properties of the phantom can be tailored to the specific application of the phantom.

For example, if the phantom is to be used as a diagnostic training aid, then incorporating material in the phantom that has particularly good imaging properties is beneficial.

Likewise if the training aid is to be used as a surgical training aid, then the elastic modulus of the tissue can be selected to correspond to the organ's elastic modulus of the corresponding tissue found in the organ and the elastic modulus of e.g. a tumor embedded therein is selected such that it feels like a tumor, e.g. comprises material that is denser than the tissue-like material forming the bulk material of the phantom.

Preferably the material that has the at least one tissue like property and/or the material forming the second structure comprises a mixture that forms a homogenous or an inhomogenous mixture that reproduce further features of the tissue of the organ, e.g. absorbance, scattering of electromagnetic radiation or acoustic waves, or its visual appearance.

Such properties can be detected using imaging devices, such as an MRI, a CT scanner and an X-ray device or an ultrasound device.

Advantageously the present invention also encompasses a method of making a mold for the first structure in order to make the at least one first structure, with the first structure having a shape that resembles the shape of at least one cavity and of the interior of a plurality of branches connected to the at least one cavity for a method of making a phantom. This method can advantageously be used in combination with the previously described method.

In any event the method of making a mold for the first structure comprises the steps of:
  producing a positive plug of the first structure, e.g. using a 3D printer;
  coating the positive plug with an elastic material, e.g. Dragon Skin®, Rebound® (Smooth-on Inc., US), to form a first structure mold that once cured maintains an outer counter of the positive plug;
  mechanically removing the cured first structure mold, e.g. by peeling the first structure mold off of the first structure;
  filling the first structure mold with a material to form the first structure, e.g. a wax material; and
  removing the first structure from the first structure mold, e.g. by peeling off the first structure mold from the first structure.

In this way an anatomically correct insert can be provided in order to produce an anatomically correct phantom. The positive plug can likewise be designed in accordance with data obtained using a CT scanner or other imaging data as explained in the foregoing.

In a further aspect the present invention relates to a phantom comprising at least one region having at least one tissue like property and at least a first cavity having a plurality of hollow branches connected thereto, the phantom being obtainable by a method of producing a phantom in accordance with the teaching presented herein.

The advantages explained in the foregoing in relation to the method are likewise true for the phantom.

In this connection it should be noted that the material of the tissue forming the first region of the phantom is preferably water soluble and is e.g. made by agarose gel.

It is preferred if the phantom that resembles a human or animal organ or tissue, comprises at least one region having at least one tissue like property and at least a first cavity having a plurality of hollow branches connected thereto, with at least some of the plurality of hollow branches being formed within the at least one region having tissue like properties, wherein the plurality of branches connected to the first cavity are produced with an average root mean square error of less than 2 mm, preferably of less than 1 mm and most preferably of less than 0.6 mm.

Such a phantom comprises internal structures that are formed with a never seen before anatomical correctness. The balloons used e.g. in the prior art have minimum size dimensions in the region of 2 mm and hence can never produce a structure having an average root mean square error of less than 2 mm. The structures disclosed herein are believed to have an order of magnitude better resolution than those in the prior art.

Advantageously the first structure is designed on the basis of data obtained from a CT scanner scanning a real organ and the finished first structure and/or phantom is likewise scanned using a CT scanner, with the image data of the scanned first structure or phantom being compared to the image data used to design the first structure in order to obtain data on the average root mean square error. In this way the limit to the resolution of the first structure is the limit of the resolution of the CT scanner used to scan the real organ and to subsequently design the first structure.

At the same time the comparison shows that the materials used to configure the phantom have good radiological properties as these can be recognized and analyzed using a CT scanner.

Preferably the material that has the at least one tissue like property is selected such that the at least one tissue like property reproduces at least one of a mechanical property, an imaging contrast in MRI, CT, X-ray or Ultrasound, an optical property, a visual appearance, a tissue's or organ's absorbance of electromagnetic radiation, a tissue's or organ's absorbance of acoustic waves, a haptic property of the tissue or organ, and an elastic modulus of the corresponding tissue found in the organ.

Advantageously the material of the first structure is water insoluble, e.g. a wax, and the material having the at least one tissue like property is water soluble, e.g. agarose gel.

In this way the shape of the cavity is defined by a wax. In this connection it should be noted that for a kidney phantom the shape of the first structure corresponds to that of the ureter, the renal pelvis and at least some of the major and minor calyxes connected thereto.

It should also be noted that the second structures for a kidney phantom can be designed to form the renal vein and the renal artery which then branch of into the interlobular vein and the interlobular artery respectively.

Preferably the at least one material of the first region is selected from the group of members consisting of polymers, EcoFlex®, agarose gel, gelatin, collagen, elastin, PEG (Polyethylene glycol), PDMS (Polydimethylsiloxane), and combinations thereof.

Preferably the kidney phantom can also comprise a third structure such as a tumor or kidney stone. If a kidney phantom is then provided that comprises the ureter, the renal pelvis and the major and minor calyxes connected thereto, as well as the renal vein and the renal artery which then branch of into the interlobular vein and the interlobular artery, the surgical training aid can be connected to different fluid supplies, mimicking the function of these fluid conducting structures and a surgeon or medical student can then perform e.g. tumor removal surgery on a kidney phantom that has fluids being conducted therein. If the surgeon or medical student then severs one of these structures a fluid will leak from the kidney phantom and will then have to be blocked during the training exercise.

In this connection it should be noted that it is advantageous if e.g. the tumor material is doped with an agent that indicates the presence of a tumor so that following the training exercise one can analyze whether sufficient tumor material was removed from the phantom.

Advantageously the phantom is selected from the group of members consisting of: a model for a human or animal heart, a brain, a lung, a kidney, at least one blood vessel, a liver, a pancreas, a gall bladder, a GI tract, a urinary tract, a testicle, a penis, a female reproductive tract, a breast, a prostate and an ear.

Figure 4:
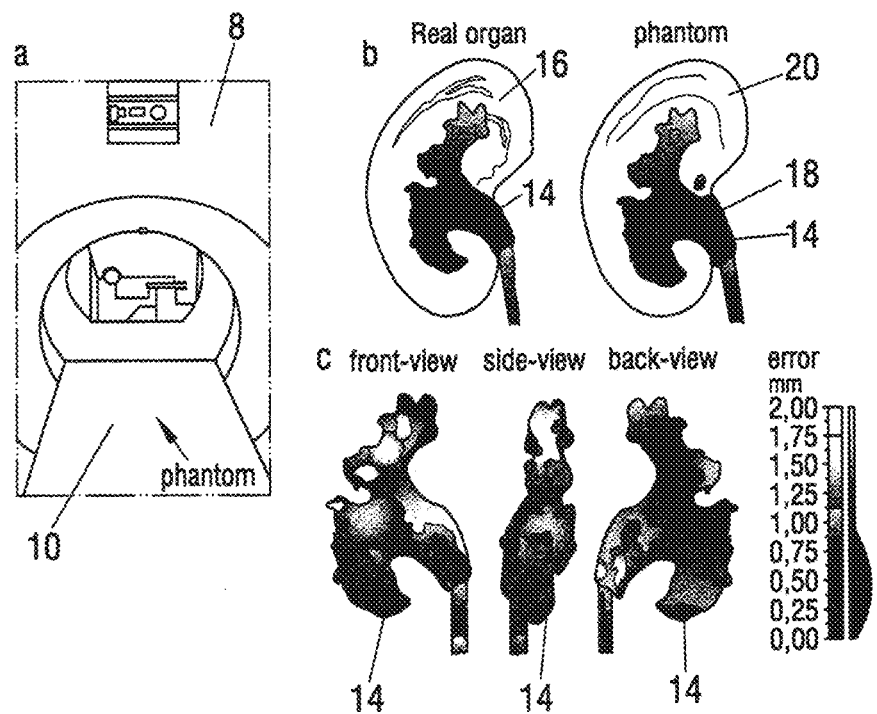
Figure 6:
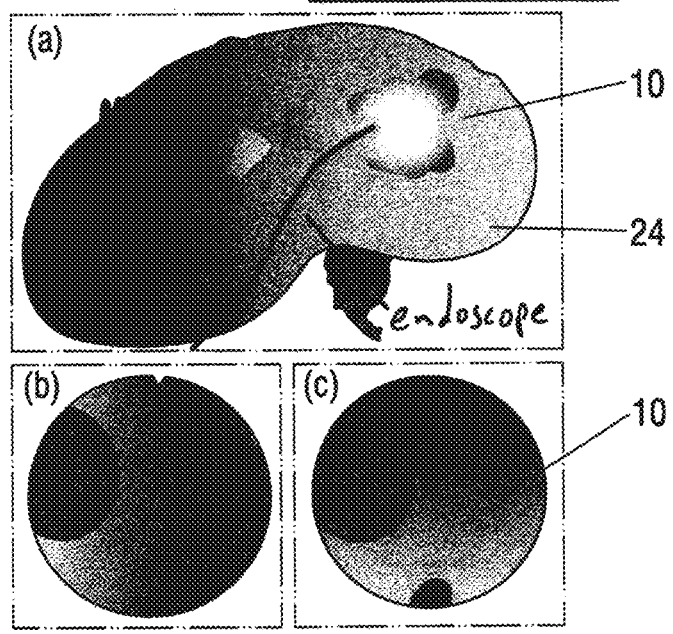
Figure 11:
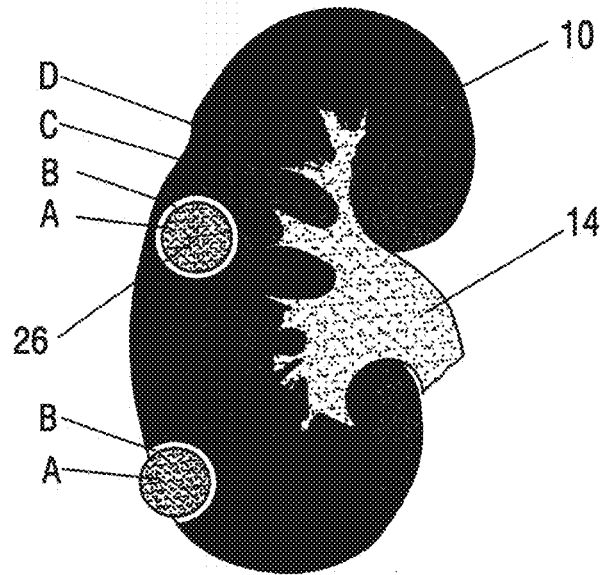
Figure 12:
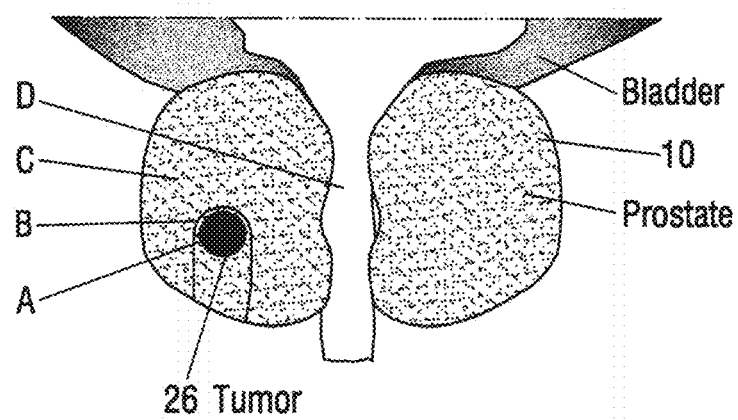
Figure 13:
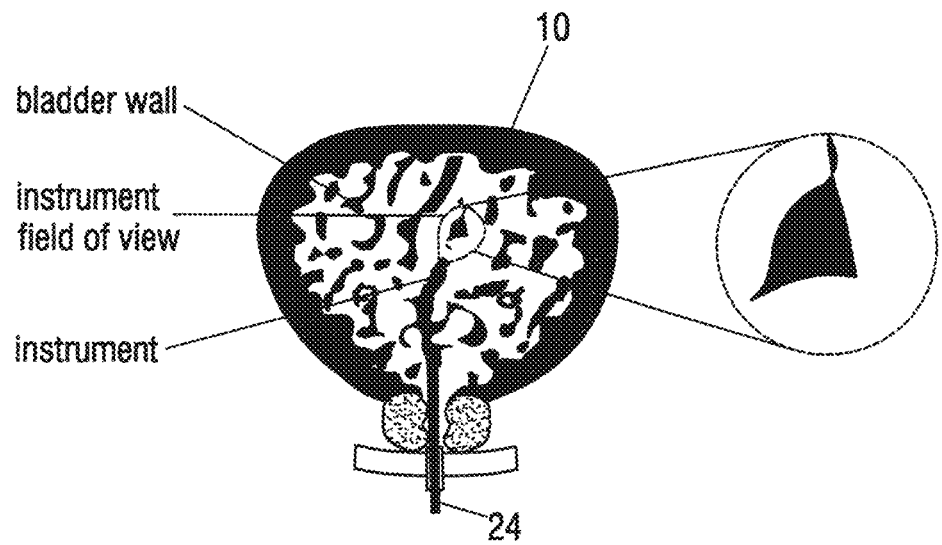
Figure 14:
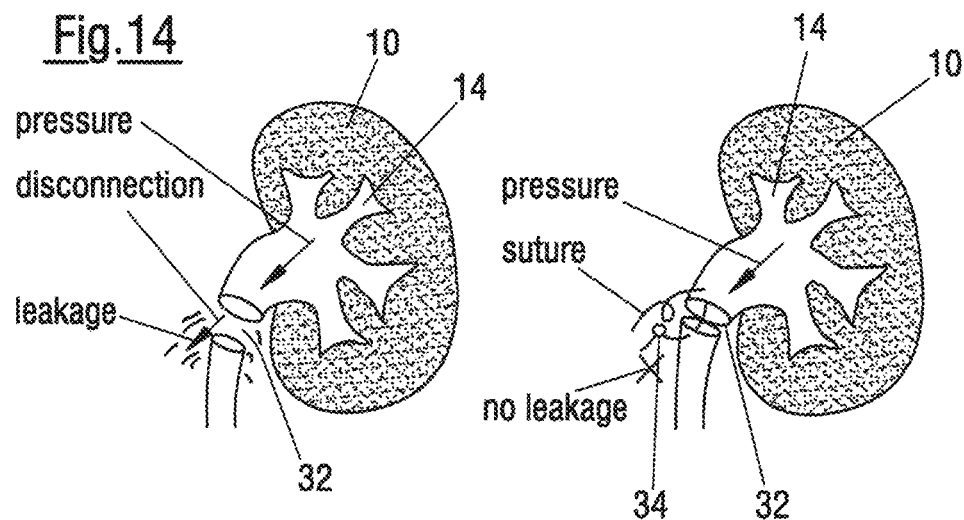

Further embodiments of the invention are described in the following description of the Figures. The invention will be explained in the following in detail by means of embodiments and with reference to the drawing in which is shown:

FIGS. 1a to d a flow chart detailing the steps required to design a mold for an anatomically correct kidney phantom;

FIGS. 2a to f a workflow for building a 3D kidney phantom;

FIGS. 3a to c respective images of the kidney phantoms made of different kinds of materials (front and back side);

FIGS. 4a to c steps carried out to evaluate the accuracy of the phantom structure;

FIGS. 5a to d ultrasound images of the three models made of different kinds of materials in comparison to a real human kidney;

FIGS. 6a to c images showing a response behavior of the kidney when an endoscope is inserted therein;

FIGS. 7a to c a flow chart showing the steps required to embed a tumor and a stone in the kidney model;

FIGS. 8a to c images showing the removal of a renal tumor from the soft kidney phantom;

FIGS. 9a to e schematic images of a glove mold method;

FIGS. 10a to d images of steps carried out in the glove mold method;

FIG. 11 a further kind of phantom comprising a transition region between a first region and a second region;

FIG. 12 a further kind of phantom;

FIG. 13 a view of an endoscopic procedure being conducted on a bladder phantom; and FIG. 14 a further view of a kidney phantom subjected to a surgical procedure.

In the following the same reference numerals will be used for parts having the same or equivalent function. Any statements made having regard to the direction of a component are made relative to the position shown in the drawing and can naturally vary in the actual position of application.

FIG. 1 shows a flow chart detailing the steps required to design a mold for an anatomically correct kidney phantom 10 (see FIG. 2). In a first step an X-ray computed tomography (CT) image 12 of a human kidney was taken (see FIG. 1a). In order to do this an iodinated contrast agent (iodine concentration of 400 mg/ml, Imeron 400; Bracco S.p.A., Milan, Italy) was injected into a collecting system of the kidney via a silicone tube connected to the ureter (all not shown). Thereafter, the cadaveric kidney was scanned using a CT scanner 8 (see FIG. 4a) (Somatom Definition Flash; Siemens Healthcare, Forchheim, Germany) with a spatial resolution of 0.3 mm. The data was reconstructed out of the axial plane with a matrix size of 512×512, and a field of view of 154 mm×154 mm. The data obtained on scanning can be stored in so-called DICOM files. These files can then be used in order to analyze the different scans taken with the CT scanner 8.

The DICOM files obtained from the CT scan were subsequently imported into computer program having the name InVesalius 3.0.0 (currently available on http://www.cti.gov.br/invesalius/). As shown in FIG. 1a, the kidney has two distinct regions, the collecting system 14 and the surrounding tissue 16. These two regions 14, 16 can easily be distinguished from one another in the CT scans due to the large contrast between the different materials of these parts of the kidney. The collecting system 14 in the center appears different in color from the kidney tissue 16 because of the concentrated contrast agent, with the background being shown in black. The data from these two regions 14, 16 of the kidney was separated in order to calculate and construct an inner mold or insert 18 (FIG. 1c) and an outer mold 20a, b (FIG. 1d) respectively for the kidney phantom 10. The surfaces for each part were exported as so-called STL files respectively, as shown in green and red in FIG. 1b.

FIG. 1c shows the insert 18 which is an anatomically correct mold of the collecting system 14 for the kidney phantom 10. In contrast to this FIG. 1d shows a mold 20a, b for an outer shape of the kidney phantom 10. This is split into two negative molds 20a, b that are separated in the middle. In order to obtain anatomically correct molds 20a, b and an anatomically correct insert 18, these were modelled using the software program Inventor 2016 (Autodesk, US). In order to produce the molds the DICOM files respectively the exported STL files were used as a starting point in Inventor 2016.

In order to produce an anatomically correct 3D kidney phantom 10, the following steps were carried out as shown in FIG. 2. The insert 18 forming the collecting system 14 was printed using an engineered wax (Solidscape® build material, this material is a mixture and the exact chemical composition is a trade secret of the company) on a 3D printer (3Z Pro, Solidscape®). The supporting wax (Solidscape® support material) was removed with petroleum at 55° C. with continuous magnetic stirring on a hot plate (not shown). The resultant insert 18 can be seen in FIG. 2a.

The outer molds 20a, b were printed with a UV curable polymer VeroClear on a 3D printer (Objet 260 Connex, Stratasys, Israel). The supporting material was removed by pressurized water jet. The respective printed halves of the outer mold 20a, b are shown in FIG. 2b. Following this the inner mold 18 was arranged in one of the two halves of the outer mold 20a (see FIG. 2c) and then the other half of the outer mold 20b was placed onto the first half of the mold 20a with a gasket arranged between the two halves of the mold 20a, b which are subsequently combined and sealed off using screws 22 to form the complete outer mold 20a, b as shown in FIG. 2d.

In order to form the kidney phantom 10 a silicone elastomer material (EcoFlex®, Smooth-on Inc., US) was mixed 1A:1B by weight on a digital balance, thoroughly mixed, degassed for 10 min, poured into the assembled mold and degassed for 30 min again in a vacuum oven. The polymer was cured at room temperature, and then it was carefully demolded from the mold 20a, b.

FIG. 2e shows the polymeric kidney phantom 10 removed from the outer mold 20a, b. The insert 18 is still present within the kidney phantom 10.

The insert 18 is subsequently removed by dissolving the wax in ethanol with a continuous magnetic stirring at 70° C. to form the kidney phantom 10 as shown in FIG. 1f. The obtained kidney phantom 10 can be attached to a silicone tube at the pelvis to mimic the ureter (not shown).

It is preferable if the material used to form the insert used in forming the collecting system 14 by way of the mold 18 has different physical or chemical properties or characteristics in comparison to the material used to form the tissue 16 in the mold 20a, b.

These different physical or chemical characteristics allow the selective removal of the material of the insert used to form the collecting system 14 while preserving the material of the tissue 16. These characteristics can be a difference in the solubility, or the melting point, or the difference in reactivity between the materials. For example, the material of the insert 18 forming the collecting system 14 is not water soluble (e.g. wax), whereas the material for the tissue 16 is water soluble (e.g. agarose). This means that water soluble materials, such as agarose, can be used to form the bulk tissue of the proposed phantom 10. This is because the insert 18 can be removed on the application of heat without the use of a solvent. This was previously not known.

In particular the material used to form the tissue 16 of the kidney phantom 10 is chosen to reproduce a property of the tissue of the real organ, such as a mechanical property, an imaging contrast in MRI, CT, or Ultrasound, an optical property or visual appearance, the tissue's or organ's absorbance of electromagnetic radiation, or a tissue's or organ's absorbance of acoustic waves, or a haptic property of the tissue or organ.

Moreover, the material used to form the tissue 16 can include a mixture that forms a homogenous or an inhomogeneous mixture that reproduces further features of the tissue 16 of the real organ, e.g. absorbance, scattering of electromagnetic radiation or acoustic waves, or its visual appearance.

In order to form a kidney phantom 10 various materials can be considered, the following none conclusive list shows exemplary materials.

1) Water based gels: agarose, gelatin, collagen, elastin, PEG (Polyethylene glycol), These are the most important materials, because they have many similar properties in comparison to human soft tissues. These are also the materials that cannot be used together with the 3D printed PVA (Polyvinylalkohol) material reported in the prior art.

2) Silicone based polymers: PDMS (Polydimethylsiloxane), EcoFlex®, Dragon Skin®

3) A mixture of several materials, such as mixing nanofibers, nanoparticles, protein or fat granules inside the water based gel to achieve tissue-like properties.

If the kidney phantom 10 is used as a surgical training tool, then a pigment or colorant can be added to the material that forms the tissue 16 in order to mimic the color of the real organ in the kidney phantom 10.

In order to test different materials the kidney phantom 10 was produced using three different kinds of materials. FIG. 3*a* shows a kidney phantom 10 made from a tissue-like silicone elastomer, FIG. 3*b* shows a kidney phantom 10 made from PDMS and FIG. 3*c* shows a kidney phantom 10 made from agarose (4%).

The respective outer shapes of the kidney phantom 10 shown in FIGS. 3*a* to *c* match that of the 3D reconstructed model. In order to confirm that the interior structure of the kidney phantom 10 indeed replicates the real kidney, a second CT scan was performed on the kidney phantom 10 with the same parameters as the real kidney. To this end FIG. 4*a* shows a photograph of the kidney phantom 10 prior to being inserted into the CT scanner 8. From a radiological point of view both the renal pelvis and all calyces corresponded to the respective structures of the CT image 12 of the cadaveric kidney as shown in FIG. 1*a*. Moreover, the CT reconstruction showed that the molding process successfully reproduced morphological details of the collecting system 14 down to sub-millimeter structures. The resolution achieved was limited by the resolution of the original CT scan. From the reconstruction of the 3D model, it is clear that the inner and outer surfaces of the model closely represent those of the original organ. This is shown in FIG. 4*b*.

FIG. 4*c* shows a quantitative error analysis of the collecting system in the phantom, comparing with the original CT scan. In order to quantitatively assess the difference between the real organ and the kidney phantom 10 a quantitative comparison was carried out using the STL files obtained for both the real kidney and the kidney phantom 10. This comparison was conducted using the software CloudCompare v2.6.1 (currently obtainable at http://www.danielgm.net/cc/).

Two separate meshes were defined in the STL files, i.e. a mesh of the phantom and a mesh of the real organ. These two meshes were then manually aligned by selecting three marker points in each mesh (typically at the tip positions of the kidney/kidney phantom 10). After the definition of each of the three marker points the software overlays the scans of the real organ and of the phantom, such that a so-called a Cloud/Cloud distance can be computed for the two vortices with an Octree level that equals 6, with the Octree level being definable in the CloudCompare software. The thereby obtained distribution of the error in distance of the elastomer model is displayed in the legend depicted in FIG. 4*c*.

The results show a maximum error of 2 mm with respect to a comparison of the medical imaging data used to construct the insert 18 forming the collecting system 14. The mean error over the total collecting system 14 (with a bounding box dimension of approximately 7 cm [length]×4 cm [width]×3 cm [height]) is 0.5 mm (FIG. 4*c*). Thus, the mean error of the model is about 1%, which is suitable for endoscopic training and testing purpose. The reconstruction and comparison of the other two materials show similar precision with about 0.5 mm mean distance error.

Likewise an average root mean square error of the tissue 16 formed in the mold 20*a, b* is less than 5 mm when compared to the medical imaging data used to design the mold 20*a, b*.

Figure 5:
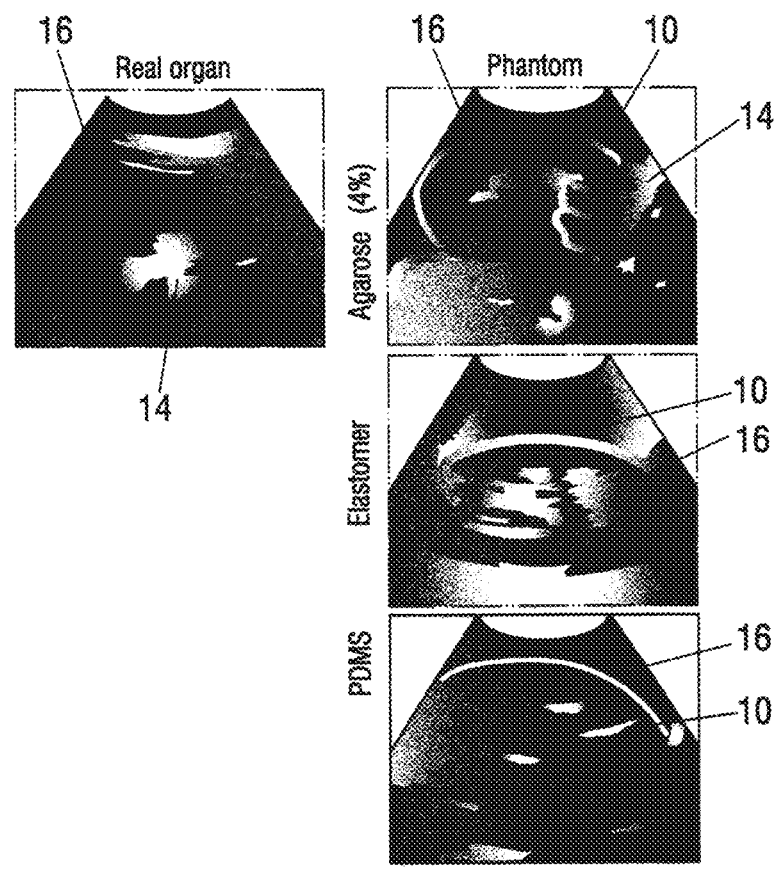

In order to test the performance of materials used to form the kidney phantom 10, ultrasound images of the three different kinds of kidney phantoms 10 were compared with a real human kidney (shown in FIG. 5A). The ultrasound image relating to the agarose model shown in FIG. 5B shows that the structures of the collecting system 14 and of the kidney tissue 16 can be recognized more clearly than those of the kidney phantom 10 made from silicone elastomer (FIG. 5C) and also those of the kidney phantom 10 made from PDMS (see FIG. 5D), Surprisingly the collecting system 14 and the tissue 16 of the agarose kidney phantom 10 can also be more clearly recognized than those of the real organ (FIG. 5A). This difference can be explained by the differences in the elasticity of the materials used for the various kidney phantoms 10, the models made of silicone elastomer and PDMS displayed a strong signal at the outer surface, however, only a white outline of the phantom 10 can be seen.

Furthermore, an endoscopic assessment was performed using a conventional flexible ureterorenoscope. On the inside of each kidney phantom 10, a smooth surface that represents the typical morphological characteristics of the upper urinary tract was visualized endoscopically (FIGS. 6*a* to *c*). The complete collecting system 14 appeared visually identical to a human kidney. All calyxes were easily intubated with the 10-French flexible ureterorenoscope. The spatial orientation of the instrument was clear at all times.

FIG. 6*a* shows a view of an endoscope 24 positioned inside the transparent kidney phantom 10. FIG. 6*b* shows an endoscopic view of an upper calyx in the human kidney and FIG. 6*c* shows the same endoscopic view in the kidney phantom 10. The fact that the position of the endoscope 24 can be tracked by eye is useful for a surgeon training to conduct such medical procedures on a kidney phantom, as he can, on the one hand, see how the endoscope 24 reacts when he initiates a movement thereof. On the other hand, he can directly compare the behavior of different endoscopes (not shown) when examining one and the same kidney phantom 10. In this way the kidney phantom 10 can form part of an assessment tool used in the training of medical personnel.

The major advantage of this work, when compared to current urological teaching and training systems and other previously reported 3D printed kidney models, is that the present method of manufacture permits a wider variety of materials to be used. The reported elastic modulus for porcine kidney is 48.56±7.32 kPa. To this end table 1 summarizes the materials properties of the three molding polymers used to build the three different kinds of kidney phantoms 10 discussed herein compared to the 3D-printable material TangoBlackPlus® (Stratasys, Eden Prairie, Minn., USA).

It was found that the elastic modulus of TangoBlackPlus® was approximately 20 times higher than that of real kidney tissue. In addition, the material was completely opaque. The silicone rubber elastomer had an elastic modulus of 60 kPa, which was very close to that of real kidney tissue. PDMS (Sylgard 184, Dow Corning) is a popular polymer that shows excellent optical transparency. This facilitates a clear visualization of the collecting system 14 inside the kidney from outside, which could also be valuable for medical education and endoscopic training. However, the elastic modulus of PDMS is much larger than that of real kidney tissues. Agarose gel is a polysaccharide polymer material that is easy-to-prepare and biocompatible, thus it has been widely used as a material to mimic soft tissues for magnetic resonance imaging (MRI) and ultrasound imaging.

Table 1 shows a comparison of the mechanical properties of the three polymers used to replicate kidney tissue, as well as, TangoBlackPlus® (a directly 3D printable material).

| Materials | Kidney tissue | Elastomer | Agarose gel (4%) | PDMS | TangoBlackPlus ® |
|---|---|---|---|---|---|
| Shore hardness | — | 20 (type 00) | 60~70 (type 00) | 44~54 (type A) | 26~28 (type A) |
| Elastic modulus (kPa) | 49 | 60 | 49 | 1320~2970 | 965~1051 |
| Tensile strength (MPa) | 4~9 | 1.1 | 0.3~0.5 | 3.51~7.65 | 0.8~1.5 |

Thus, depending on the application of the kidney phantom 10 a different kind of material of the kidney phantom 10 can be made available. For example if the kidney phantom 10 is to be used for imaging purposes a phantom made of Agarose gel would be a good choice. In contrast to this if a surgical evaluation of the kidney phantom 10 is to be performed a kidney phantom 10 made from an elastomer or PDMS may be the better choice due to the tensile strength of these materials.

In order to form a kidney phantom 10 that can be used to train medical personnel in the removal or detection of e.g. a tumor or a stone from a kidney a second feature 26 could be embedded into the kidney phantom 10.

In spite of the hollow collecting system 14 in the kidney, other anatomical important structures can be also embedded with the same molding method. FIGS. 7a to 7c show the schematic of the workflow of embedding a tumor 26 and a kidney stone 27 in the kidney phantom 10.

The kidney stone 27 is incorporated in the phantom 10 by including a material mimicking a real kidney stone in the collecting system 14 formed by the insert 18 during the fabrication process of the insert 18. Alternatively a cavity could be provided in the insert 18 on a manufacture thereof and this cavity could subsequently be filled with the material mimicking a real kidney stone. In such a way a larger sized stone can be placed within the calyx with a small opening to the collecting system 14 and can then be used in the surgical procedures associated with the removal of a kidney stone, e.g. by means of lithotripsy.

First, two features, i.e. the collecting system 14 and the tumor 26 were prepared respectively as shown in FIG. 7a. The tumor 26 was made by molding PDMS material in a separate 3D printed mold. An important anatomical detail about the common renal tumor is that it is neither in contact with the outer surface of the kidney, nor in contact with the collecting system 14. In other words, the tumor 26 should be fully surrounded with normal tissue 16. In order to reproduce this anatomy, the tumor 26 is inserted into a further 3D printed negative mold (not shown), which has the same shape as part of the final outer mold 20a, b. Thus a tumor insert 28 comprising the tumor 26 that is encased by tissue 16 is formed in the negative mold for the tumor insert 28. This tumor insert 28 has an outer contour that fits exactly in shape with part of the outer shape of the final mold 20a, b.

After assembling the collecting system 14 and the tumor insert 28 comprising the tumor 26 in the final outer mold 20a, b (FIG. 7b), the mold is filled with liquid polymer to form the tissue 16. When the polymer solidifies, it will connect as one whole piece with the same material of the tissue 16 surrounding the tumor 26 formed in the further mold 28 (FIG. 7c).

Figure 8:
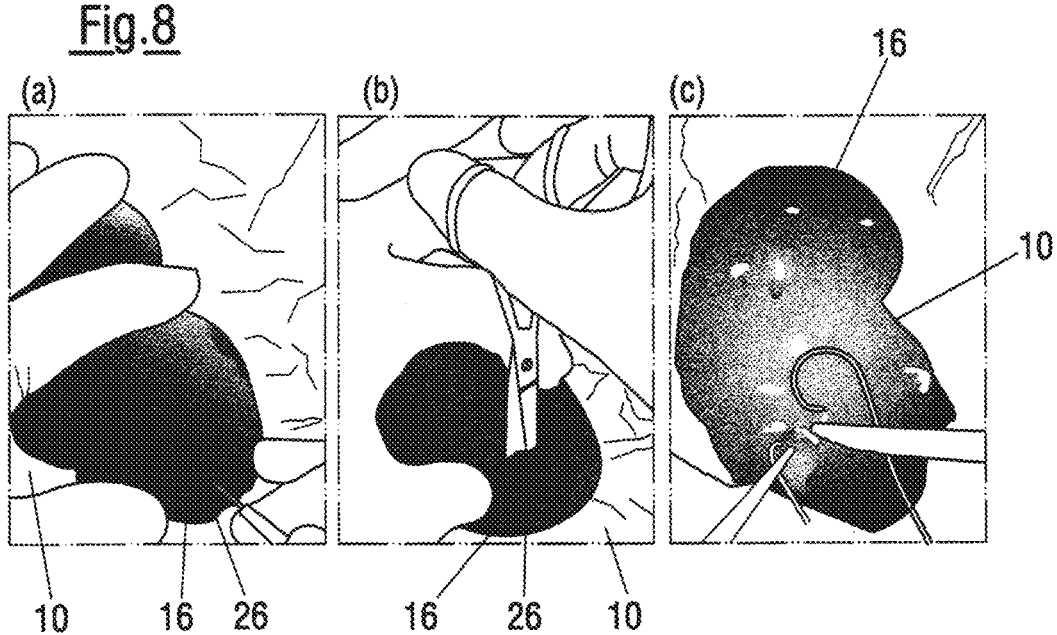

In this way, the tumor 26 can be inserted at any exact pre-defined "suspended" position inside the kidney phantom 10. One important application of the constructed kidney phantom 10 having a tumor 26 is illustrated in FIG. 8, as a training model for tumor removal using open or laparoscopic surgery techniques.

Moreover, knowing the precise position in advance means that the kidney phantom 10 having a tumor 26 can be used to calibrate imaging devices, such as MRI, CT scanner 8, X-ray, and Ultrasound and/or to assess a medical personnel operating such an imaging device.

Similar methods can also be used to embed other important anatomies, such as blood vessels and nerves into a kidney phantom 10.

FIGS. 8a to c show images showing the removal of a simulated renal tumor 26 from the soft kidney phantom 10. FIG. 8a in this regard shows the cutting of tissue 16 in order to access the simulated renal tumor 26. Following the access to the tumor 26 it can be exposed and removed as seen in FIG. 8b. Thereafter the kidney phantom 10 can be repaired by suturing as is shown in FIG. 8c.

In order to now assess whether medical personnel has removed the correct amount of tumor 26 from the kidney phantom 10, the tumor 26 and/or the kidney phantom 10 can respectively comprise some form of contrast agent that indicates the presence of the tumor 26.

The contrast agent could, for example, be a phosphorescent kind of material that glows in the dark so a quick comparison of the material removed with that left behind in the kidney phantom 10 by turning off a light indicates whether sufficient tumor material has been removed.

In other instances the contrast agent can comprise materials sensitive to UV light, so a black light could be used to assess the presence of any tumor remnants in the phantom 10 and hence the performance of medical personnel carrying out a performance test.

In other instances materials that can be imaged particularly well using one of CT, MRI and Ultrasound could be embedded in the kidney phantom 10 and/or the tumor 26 such that one of these imaging techniques could be used to analyze and asses the performance of someone removing the tumor 26 from the kidney phantom 10.

In yet other instances two contrast agents can be embedded for different imaging modalities, e.g. the combinations of CT, MRI, PET, Ultrasound, x-ray and/or fluorescence; and/or two contrast agents can be embedded for the same imaging modality but for different imaging sequences, e.g. for an intensity sequence and a pulse sequence in MRI.

In any event one can also dope the material of the tissue 16 with a contrast agent or like material that can be visualized to see if too much or too little tissue has been removed from the kidney phantom 10. In this way a medical personnel training with the kidney phantom 10 can be given direct feedback about whether the medical procedure which removed the tumor 26 also removed too much or too little tissue surrounding the tumor cite.

In a similar way the comparison can also see how much tissue was removed in order to see if a sufficient amount of tumor 26 was removed from the kidney phantom 10.

In this way one can also assess the performance of a human or robot carrying out a medical imaging procedure by using a phantom resembling a human or animal organ or tissue. In this case the kidney phantom 10 can be provided with a target region, simulating a tumor, a kidney stone, a bone fragment, a bullet or a bullet or knife wound at a pre-defined position with a pre-defined size. Thereafter a diagnostic procedure is carried out to determine the position and/or extent of the target region. The assessment is then carried out by comparing the diagnostic result with the known size and position of the target region. In this connection it should be noted that the diagnostic procedure is one of ultrasound, by MRI, by CT and/or by X-ray imaging, PET.

Rather than including a tumor 26 in the kidney phantom other structures could additionally be included in the kidney phantom 10. These can be selected from the group of members comprising e.g. a cavity, at least one blood vessel, at least one nerve, a kidney stone, a prosthesis or a medical implant.

In order to produce the insert 18, a so-called glove mold process can be used for a mass production of the kidney phantom 10, i.e. of an anatomical structure.

The glove mold process works as an alternative for the 3D wax printing method to make the positive plug 18a (insert) of the collecting system 14. As the wax 3D printing is time-consuming and expensive. FIG. 9 illustrates the workflow of this method. First, a positive plug 18a is obtained by 3D printing a UV curable polymer (see FIG. 9a and FIG. 10a), which is a hard plastic material and does not easily dissolve in solvent or melt with temperature as the wax materials mentioned above do. Then, 3 to 5 layers of a glove mold material 30 are applied to the positive plug 18a, in the present instance is brushed onto the positive plug 18a as shown in FIG. 9b.

Once the glove mold material 30 is cured, the glove mold 30 can be peeled off as it is soft and stretchy as shown in FIGS. 9c and 10b respectively. This glove mold 30 can then serve repeatedly as a mold for the insert 18 forming the collecting system 14 of a kidney phantom 10 as shown in FIG. 9d. This glove mold 30 can be used to mold the collecting system 14 using materials, such as paraffin and gelatin as shown in FIGS. 10c and 10d respectively. In this way multiple anatomical features can be replicated precisely, fast and cost-effectively as is schematically indicated in FIG. 9e by the plurality of inserts 18.

Figure 7:
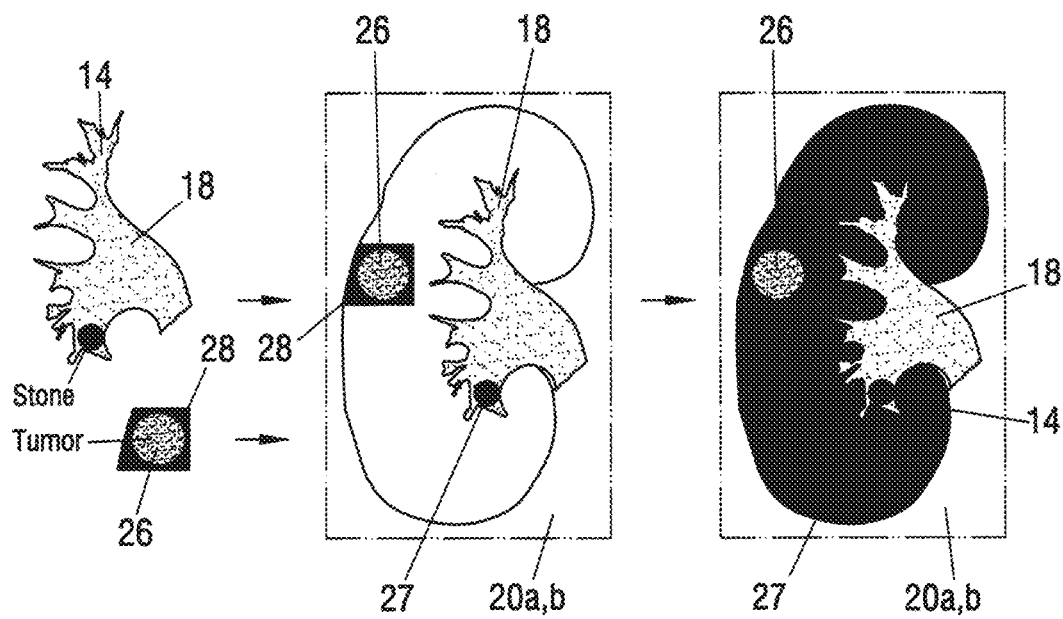

The glove mold method can also be used to make other anatomical structures, such as the tumor 26 mentioned above. However, the restriction to this method is that the molded shape cannot contain any closed loop, thus it will not be a suitable method for structures such as blood vessels and nerves. The glove mold method can also be used to make one part of the phantom (e.g. the collecting system 14), which can then be assembled with other parts that are made by other techniques (e.g. 3D printing of the blood vessels) in order to mold the final kidney phantom 10 with multiple anatomical features (similar to what is shown in FIG. 7), in order to produce even more sophisticated kidney phantoms 10. These can then be connected to fluid conveying devices to mimic the flow of blood and possibly of other liquids. In use of these sophisticated kidney phantoms 10, a surgeon is given direct feedback on whether he or she cut e.g. a blood vessel of the kidney phantom 10 or not.

The foregoing description relates to a kidney phantom 10. However, it should be noted that phantoms of various other organs could be produced and used for training purposes. These animal or human organ phantoms include, but are not limited to the liver, the intestine, the prostate, the lungs, the brain and the heart, blood vessel, pancreas, gall bladder, GI tract, urinary tract, testicle, penis, female reproductive tract, breast, and an ear. The surgery at all of these organs is conducted by highly skilled medical staff and the production of comparatively cheap phantom organs makes available a comparatively low cost training and assessment tool that can be used in training the medical personnel.

Having regard to e.g. a prostate, a bladder or a heart phantom, part of the phantom can include a pump or material forming a pump to mimic the behavior of the real organ in an improved way during a training exercise.

Moreover, the material of the tissue of the phantom used has an elastic modulus that corresponds to the organ's elastic modulus of the corresponding tissue found in the organ.

It should also be noted that sensors (not shown) could be incorporated into the phantom 10 described herein. These sensors could include physiological markers embedded within the phantom 10. Using these sensors, signals, such as the blood flow/pressure, fluidic flow, tissue intactness, tumor removal rate etc., could be evaluated from the phantom 10. This evaluation could be done in real time through the use of the sensors or offline in a CT scanner 8 or an MRI device etc.

In this regard it should be noted that if a liquid or fluid is conducted through one or a plurality of cavities provided in the phantom 10, then the presence (leaking) of that fluid could be used as a real time sensor signal to indicate that something has gone wrong during the surgery on the phantom 10.

Likewise sensors could be embedded in parts of the phantom resembling nerves and on cutting these nerves an audible sound could be emitted to indicate that nerves have been severed or punctured.

FIG. 11 shows a further kind of kidney phantom 10 comprising a transition region B that surrounds a second region A that can, for example, be a tumor. This transition region B separates the tumor A from the normal tissue C present within the phantom 10. In this way a structure forming the tumor A can be introduced into the tissue-like material with the transition zone B present at the interface between the first and second regions A and C. This transition zone can comprise a mixture of the respective materials of the first and second regions A and C. Alternatively this transition zone B can also comprise different material properties from those of regions A and C and provision can then for example be made that only this transition zone comprises the material that can be visualized as a successful completion of the surgical exercise could be the complete removal of this transition zone B.

FIG. 12 shows a further kind of phantom 10, namely a phantom of a prostate. Like the phantom 10 depicted in FIG. 11, a further structure, e.g. a tumor, is inserted in a region marked A. This structure is surrounded by a region comprising material B and can be embedded in a first region comprising material C.

Both of the phantoms 10 of FIGS. 11 and 12 can also comprise further regions D that can model structures of the specific organ. In FIG. 11 region D corresponds to a collecting system 14 of a kidney, whereas in FIG. 12 region D corresponds to a urethra.

In some cases, the target of the medical procedure is to completely remove the region A, maintain the maximum volume of region B and absolutely no removal of region C (according to the kidney tumor removal of FIG. 11). In other cases the target could be the removal of both regions A and B while maintained region C.

It should further be noted that if one of the respective phantoms 10 shown in FIGS. 11 and 12 are used for the assessment of a medical procedure, then the medical procedure can be the removal of tissue for the purpose of a biopsy. The aim being the removal of a small amount of only material A. Depending on the assessment criteria the removal of only material A could lead to a positive assessment, whereas the removal of only material C could lead to a negative assessment etc.

It should be noted that where reference is made to a tumor in the foregoing, the second structure 26; A, B introduced into the phantom 10 could also replicate diseased tissue and/or an anomalous structure present in the organ and as such may either be partly removed for the purpose of biopsy, i.e. a diagnostic purpose, or completely removed by means of a medical procedure.

It should also be noted that the phantom 10 is provided to allow a medical professional or a robot to practice cutting techniques on a simulated organ rather than on a real organ which are hard to come by and hence expensive. These different cutting techniques can range from simple cutting and suturing practice for medical students to practicing biopsies at regions hard to reach and or tumor removal at sensitive positions. Generally speaking these hard to reach positions cannot be simulated using real organs as these are generally very specific cases of application.

FIG. 13 shows a view of an endoscopic procedure being conducted on a bladder phantom 10, with an enlarged field of view of the endoscope 24 being shown in the circle. By moving the endoscope 24 at the point of assessment an approximately 360° view of the point of assessment can be obtained for the endoscope 24 in question.

The assessment of the medical procedure can then be a measurement of the viewing field scanned by the medical personnel or robot. In order to do this the phantom 10 may further comprise an optical pattern embedded therein, more specifically embedded in the target region 26. This optical pattern then conveys information relating to the position and size of the target region. This information is either optically invisible to the endoscope 24 or cannot be interpreted by the operator, but can be analyzed using specific filters in software provided for the assessment of the medical procedure. On reviewing this information a surface area of any scan taken can be made and compared to a surface area that is obtainable by that specific device. In this way one can assess if the medical personnel or robot has detected the complete target region respectively a surface area thereof or not.

In this way a further assessment parameter is the completeness (surface area coverage) with which for instance an imaging or inspection has been performed. For instance in bladder cystoscopy (inspection) it is important that, during an endoscopic cystoscopic procedure, the entire inside of a bladder is inspected and that no region is missed, as this could for instance mean that the inspection misses a tumor.

FIG. 14 shows a further view of a kidney phantom 10 subjected to a surgical procedure. On conducting the medical procedure the ureter is severed at a point of severance 32. This point of severance 32 needs to be repaired in order to repair the kidney phantom 10. This repair is conducted by suturing the ureter using a suture 34. The quality of this suture 34 can then also be assessed as part of the review of the medical procedure. This can for example be done by: a measurement of a mechanical strength of the suture, and a subsequent comparison with a target value; a measurement of the pressure of the phantom after the intervention, possibly by a comparison of pressure before and after, and a comparison with a target value; a measurement of the elasticity of an implant or a connection; a measurement of an electrical connection in case of a simulated neuronal connection; and a test to see if an implant or device embedded during the medical procedure functions correctly.

The invention claimed is:

1. A method of producing a phantom resembling a human or animal organ or tissue, the phantom comprising at least one first region having at least one tissue like property and at least one cavity having a plurality of hollow branches connected thereto, with at least some of the plurality of hollow branches being formed such that they project into the first region having tissue like properties, the method comprising the steps of:
   making at least a first structure having an average root mean square error of less than 2 mm and a shape that resembles the shape of the at least one cavity and of the interior of the plurality of branches connected to the at least one cavity;
   placing said first structure in a phantom mold having an inner shape that resembles an outer shape of the phantom;
   filling the phantom mold with a material that has the at least one tissue like property to form the phantom; and
   removing the first structure from the phantom in order to form the one cavity having a plurality of hollow branches connected thereto within the phantom, the phantom having both an anatomically correct outer shape and an anatomically correct inner shape.

2. The method in accordance with claim 1, further comprising the steps of:
   providing at least one second structure in the phantom mold, with the at least one second structure being selected from the group of members consisting of at least one tumor-like material, tissue-like material, a transient region, at least one stone, at least a bone, structures that form at least one blood vessel or a network of interconnected blood vessels, structures that form a further cavity, models of nerves or interconnected nerves, a prosthesis or at least one medical implant.

3. The method in accordance with claim 2, wherein the material of the at least one second structure is selected as one of water insoluble and water soluble.

4. The method in accordance with claim 1, wherein the step of removing the first structure from the phantom is carried out by the application of at least one of heat, the use of a solvent, the use of mechanical force and due to a difference in reactivity between the materials used for the first structure and the material having the at least one tissue like property.

5. The method in accordance with claim 1, wherein the material of the first structure is water insoluble, and the material having the at least one tissue like property is water soluble.

6. The method in accordance with claim 1, wherein at least one of the phantom mold, and the first structure is formed using a 3D printer.

7. The method in accordance with claim 2, wherein at least one of the phantom mold, the first structure and the second structure is formed using a 3D printer.

8. The method in accordance with claim 1, wherein the first structure is formed in a mold.

9. The method in accordance with claim 2, wherein the second structure is formed in a mold.

10. The method in accordance with claim 1, wherein the material that has the at least one tissue like property is selected such that the at least one tissue like property reproduces at least one of a mechanical property, an imaging contrast in MRI, CT, X-ray or Ultrasound, an optical property, a visual appearance, a tissue's or organ's absorbance of electromagnetic radiation, a tissue's or organ's absorbance of acoustic waves, a haptic property of the tissue or organ, and an elastic modulus of the corresponding tissue found in the organ.

11. The method in accordance with claim 1,
wherein the material that has the at least one tissue like property comprises a mixture that forms a homogenous or an inhomogenous mixture that reproduce further features of the tissue of the organ or its visual appearance.

12. A method of making a phantom, the phantom comprising at least one first region having at least one tissue like property and at least one cavity having a plurality of hollow branches connected thereto formed by at least a first structure having an average root mean square error of less than 2 mm, with at least some of the plurality of hollow branches being formed such that they project into the first region having tissue like properties, the method comprising the steps of:
producing a positive plug of the first structure;
coating the positive plug with an elastic material to form a first structure mold that once cured maintains an outer counter of the positive plug;
mechanically removing the cured first structure mold;
filing the first structure mold with a material to form the first structure; and
removing the first structure from the first structure mold, the phantom having both an anatomically correct outer shape and an anatomically correct inner shape.

13. A phantom resembling a human or animal organ or tissue, the phantom comprising at least one first region having at least one tissue like property and at least a first cavity having a plurality of hollow branches connected thereto, the phantom being obtainable by a method of producing a phantom resembling a human or animal organ or tissue, the phantom comprising at least one first region having at least one tissue like property and at least one cavity having a plurality of hollow branches connected thereto, with at least some of the plurality of hollow branches being formed such that they project into the first region having tissue like properties, the method either comprising the steps of:
making at least a first structure having an average root mean square error of less than 2 mm and a shape that resembles the shape of the at least one cavity and of the interior of the plurality of branches connected to the at least one cavity;
placing said first structure in a phantom mold having an inner shape that resembles an outer shape of the phantom;
filling the phantom mold with a material that has the at least one tissue like property to form the phantom;
removing the first structure from the phantom in order to form the one cavity having a plurality of hollow branches connected thereto within the phantom; or the method comprising the steps of:
producing a positive plug of the first structure;
coating the positive plug with an elastic material to form a first structure mold that once cured maintains an outer counter of the positive plug;
mechanically removing the cured first structure mold;
filing the first structure mold with a material to form the first structure;
removing the first structure from the first structure mold; and
the phantom having both an anatomically correct outer shape and an anatomically correct inner shape.

14. A phantom resembling a human or animal organ or tissue, the phantom comprising at least one first region having at least one tissue like property and at least a first cavity having a plurality of hollow branches connected thereto, with at least some of the plurality of hollow branches being formed within the at least one region having tissue like properties, wherein the plurality of branches connected to the first cavity have an average root mean square error of less than 2 mm, and the phantom having both an anatomically correct outer shape and an anatomically correct inner shape.

15. The phantom in accordance with claim 14, wherein the first structure is designed on the basis of data obtained from a CT scanner scanning a real organ and the finished first structure and/or phantom is likewise scanned using a CT scanner, with the image data of the scanned first structure or phantom being compared to the image data used to design the first structure in order to obtain data on the average root mean square error.

16. The phantom in accordance with claim 14,
wherein the material that has the at least one tissue like property is selected such that the at least one tissue like property reproduces at least one of a mechanical property, an imaging contrast in MRI, CT, X-ray or Ultrasound, an optical property, a visual appearance, a tissue's or organ's absorbance of electromagnetic radiation, a tissue's or organ's absorbance of acoustic waves, a haptic property of the tissue or organ, and an elastic modulus of the corresponding tissue found in the organ.

17. The phantom in accordance with claim 14,
wherein the material of the first structure is water insoluble and the material having the at least one tissue like property is water soluble.

18. The phantom in accordance with claim 17, wherein the phantom is further provided with at least one second structure.

19. The phantom in accordance with claim 14, wherein the phantom is selected from the group of members consisting of: a model for a human or animal heart, a brain, a lung, a kidney, at least one blood vessel, a liver, a pancreas, a gall bladder, a GI tract, a urinary tract, a testicle, a penis, a female reproductive tract, a breast, a prostate , an ear, an eye, a nose, an appendix, a joint, a bone and a heart.

* * * * *